(12) United States Patent
Gatzemeyer et al.

(10) Patent No.: US 8,628,483 B2
(45) Date of Patent: *Jan. 14, 2014

(54) ORAL CARE IMPLEMENT HAVING A LIQUID COLLECTION SYSTEM

(75) Inventors: John Gatzemeyer, Hillsborough, NJ (US); Madhusudan Patel, Somerset, NJ (US); Elizabeth Gittins, Stewartsville, NJ (US); Harsh M. Trivedi, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/526,281

(22) Filed: Jun. 18, 2012

(65) Prior Publication Data
US 2012/0255134 A1    Oct. 11, 2012

Related U.S. Application Data

(63) Continuation of application No. 12/544,654, filed on Aug. 20, 2009, now Pat. No. 8,202,230.

(51) Int. Cl.
*A61B 10/00* (2006.01)
*A61B 5/00* (2006.01)
*A61B 17/24* (2006.01)

(52) U.S. Cl.
CPC ............................... *A61B 17/24* (2013.01)
USPC .......................................... 600/573; 600/569

(58) Field of Classification Search
USPC .................... 600/569, 573–582, 584
See application file for complete search history.

(56) References Cited

U.S. PATENT DOCUMENTS

| 2,154,209 | A | | 4/1939 | Kohn | |
|---|---|---|---|---|---|
| 4,538,631 | A | | 9/1985 | Prince | |
| 4,753,249 | A | * | 6/1988 | Muller | 600/584 |
| 5,000,193 | A | * | 3/1991 | Heelis et al. | 600/573 |
| 5,458,563 | A | * | 10/1995 | Stewart | 601/162 |
| 5,463,792 | A | | 11/1995 | Hogan et al. | |
| 5,578,023 | A | * | 11/1996 | Schneider | 604/332 |
| 5,830,154 | A | * | 11/1998 | Goldstein et al. | 600/572 |
| 5,842,248 | A | | 12/1998 | Van Grol et al. | |
| 5,910,122 | A | * | 6/1999 | D'Angelo | 600/573 |
| 6,533,734 | B1 | * | 3/2003 | Corley et al. | 600/573 |
| 6,623,698 | B2 | | 9/2003 | Kuo | |

(Continued)

FOREIGN PATENT DOCUMENTS

| EP | 0097904 | 1/1984 |
|---|---|---|
| JP | 2003250631 | 9/2003 |

(Continued)

OTHER PUBLICATIONS

International Search Report for PCT/US2009/054582 filed Aug. 21, 2009.

*Primary Examiner* — Sean Dougherty
*Assistant Examiner* — Michael C Stout
(74) *Attorney, Agent, or Firm* — Ryan M. Flandro

(57) ABSTRACT

An oral care implement includes a collection system for oral fluids. Some embodiments of the implement may include an oral care region having a wearable oral member having a thickness that is reduced during use, a reservoir for retaining an oral fluid, a receiver coupled to the oral member for receiving an oral fluid, and a fluid pathway in communication with the receiver to provide the oral fluid to the reservoir.

16 Claims, 6 Drawing Sheets

(56) References Cited

U.S. PATENT DOCUMENTS

| | | | |
|---|---|---|---|
| 6,663,679 B1* | 12/2003 | Duncan | 73/335.01 |
| 7,282,181 B2* | 10/2007 | Hudak et al. | 422/549 |
| 7,314,453 B2* | 1/2008 | Kuo | 600/584 |
| 7,449,001 B2* | 11/2008 | Stoltz | 600/582 |
| 7,845,944 B2* | 12/2010 | DiGasbarro | 433/91 |
| 2002/0127143 A1* | 9/2002 | Kuo | 422/68.1 |
| 2003/0023189 A1* | 1/2003 | Kuo | 600/584 |
| 2003/0045814 A1* | 3/2003 | Sangha | 600/573 |
| 2003/0053938 A1* | 3/2003 | Szeles | 422/102 |
| 2003/0120180 A1* | 6/2003 | Kaylor et al. | 600/584 |
| 2004/0049123 A1* | 3/2004 | Kuo | 600/551 |
| 2004/0082878 A1* | 4/2004 | Baldwin et al. | 600/573 |
| 2004/0097834 A1* | 5/2004 | Stoltz | 600/573 |
| 2004/0220498 A1* | 11/2004 | Li et al. | 600/584 |
| 2005/0221401 A1 | 10/2005 | Nomura et al. | |
| 2005/0244794 A1 | 11/2005 | Kemp et al. | |
| 2006/0141421 A1* | 6/2006 | Braunecker et al. | 433/215 |
| 2006/0225744 A1 | 10/2006 | Braunecker et al. | |
| 2007/0151575 A1 | 7/2007 | De Masi | |
| 2007/0173738 A1* | 7/2007 | Stoltz | 600/582 |
| 2007/0255177 A1* | 11/2007 | Pronovost | 600/573 |
| 2008/0098550 A1* | 5/2008 | McKay | 15/169 |
| 2009/0012425 A1* | 1/2009 | Dodge et al. | 600/572 |
| 2009/0036796 A1* | 2/2009 | Rising et al. | 600/573 |
| 2009/0132011 A1* | 5/2009 | Altshuler et al. | 607/88 |
| 2009/0197220 A1* | 8/2009 | Cindrich | 433/216 |
| 2010/0331725 A1* | 12/2010 | Libby et al. | 600/573 |

FOREIGN PATENT DOCUMENTS

| | | |
|---|---|---|
| JP | 2004108858 | 4/2004 |
| JP | 2005257604 | 9/2005 |
| WO | WO 2004/084752 | 10/2004 |

\* cited by examiner

ORAL CARE IMPLEMENT HAVING A LIQUID COLLECTION SYSTEM

CROSS-REFERENCE TO RELATED APPLICATIONS

The present application is a continuation of U.S. application Ser. No. 12/544,654 filed on Aug. 20, 2009, now allowed, the entirety of which is hereby incorporated by reference.

BACKGROUND OF THE INVENTION

The present invention pertains to an oral care implement, in particular, to a toothbrush with a liquid collection system. Tooth brushing is part of a daily oral hygiene activity. Proper dental care involves regular flossing, brushing and dental checkups. Dentists generally recommend that an individual brush his or her teeth for a minimum interval per cleaning, such as two minutes. Despite such recommendations, many individuals, especially young children, do not regularly brush their teeth for the recommended minimum interval. Such habits often can be attributed to the individual regarding tooth brushing as a mundane duty with few pleasurable aspects. Dental checkups to a dentist office are typically the only feedback a person receives on their dental cleaning efforts. There is unfortunately plenty of time in between checkups for poor dental habits to cause problems. For example, gingivitis, periodontal disease, and a host of other problems can be magnified if dental cleaning habits are not rectified promptly.

BRIEF SUMMARY OF THE INVENTION

The present invention pertains to an oral care implement having a collection system of oral fluids.

In one aspect, an oral care implement includes an oral care region having an oral member having a thickness that is reduced or shortened during use; a reservoir for retaining an oral fluid; a receiver fluidly coupled to the oral member for receiving an oral fluid; and a fluid pathway in communication with the receiver to provide the oral fluid to the reservoir. In one possible embodiment, the oral member may be made of a conventional hydrogel material that may swell during use.

In another aspect, an oral care implement includes a reservoir for retaining an oral fluid; and a multilayer collection member including a layer that wears away during use so as to expose an indicium layer that indicates when the reservoir should be provided for analysis of the collected oral fluid.

In yet another aspect, an oral care implement has a head containing tooth cleaning elements, a reservoir for storing an oral fluid. A capillary channel constructed from a fibrous material, ceramic, porous plastic, or combination thereof extends through at least a portion of the implement to receive the oral fluid from one or more inlets.

BRIEF DESCRIPTION OF THE DRAWINGS

The features, and advantages of the invention will be apparent from the following more detailed description of certain embodiments of the invention and as illustrated in the accompanying drawings in which.

DETAILED DESCRIPTION OF THE INVENTION

In the following description, the invention is discussed in terms of a toothbrush (e.g. a form of an oral care implement) but could be in the form of other personal care implements. Further, it is understood that other embodiments may be utilized and structural and functional modifications may be made without departing from the scope of the present invention.

Figure 1:
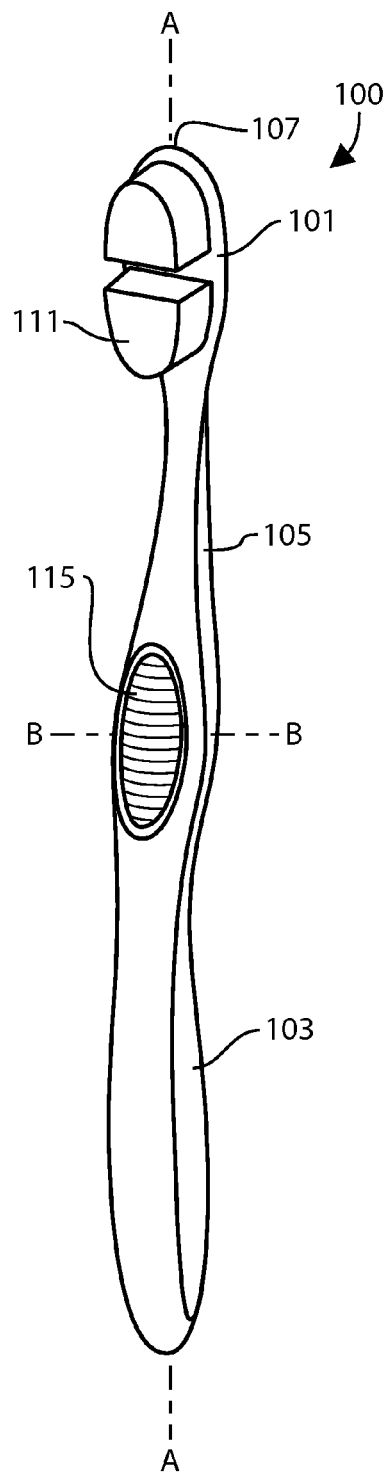
FIGS. 1 and 2 are schematic perspective front and rear views of an oral care implement, such as a toothbrush, according to one or more embodiments of the invention.
Figure 2:
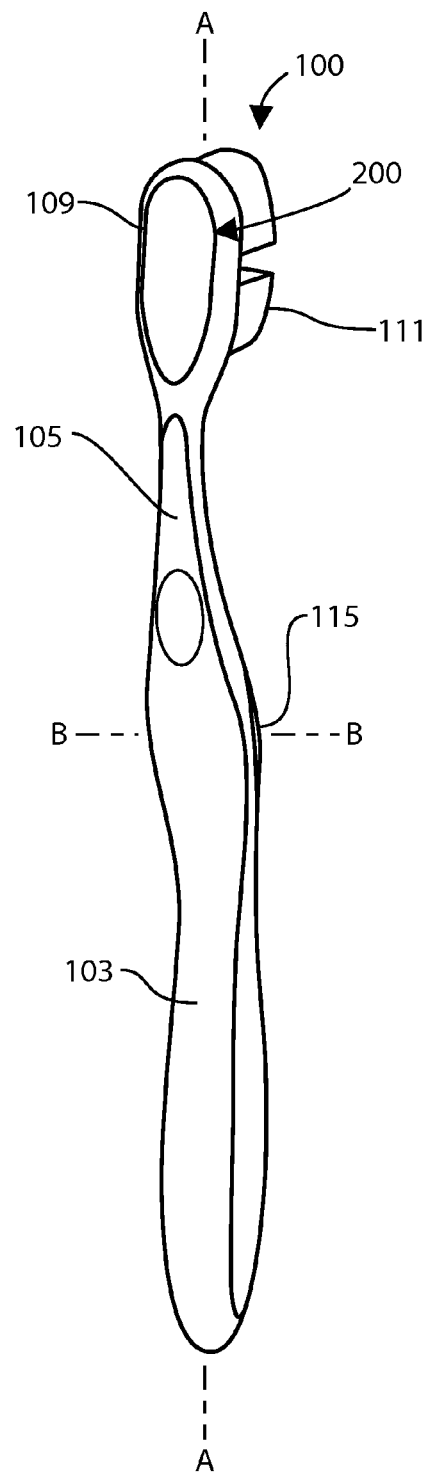

FIGS. 1-2 illustrate an oral care implement, such as a toothbrush, generally designated with the reference numeral 100. The toothbrush 100 generally includes a head 101 and a handle 103.

The handle 103 is generally an elongated member dimensioned so that a user can readily grip and manipulate the toothbrush 100. The handle 103 may be formed of many different shapes, lengths and with a variety of constructions. In one construction, the handle 103 has a neck portion 105 positioned adjacent the head 101. The neck portion 105 may be a narrowed region on the handle 103 between head 101 and the part of the handle normally gripped by the user. Nevertheless, the neck portion 101 could be the region between the head 101 and the part of the handle normally gripped by the user. In another construction, the handle 103 is integrally formed with the head 101. While the head is normally widened relative to the neck of the handle, it could in some constructions simply be a continuous extension or narrowing of the handle. Other attachment configurations also are possible.

The head 101 may include an oral care region comprising one or more tooth cleaning elements 111. As used herein, the term "tooth cleaning elements" or "cleaning elements" includes any type of structure that is commonly used or is suitable for use in providing oral health benefits (e.g., tooth cleaning, tooth polishing, tooth whitening, massaging, stimulating, etc.) by making contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members.

In one construction, tooth cleaning elements 111 are formed from a plurality of bristles. Referring to FIGS. 1 and 2, the tooth cleaning elements 111 are bristle regions having different shapes, however, it is understood that a number of different configurations of oral care implements may be utilized. The one or more tooth cleaning elements 111 may be attached to the head 101 by known methods, such as being fit within recesses formed in the head 101 along a front portion 107 of the toothbrush 100 (FIG. 1).

Figure 3:
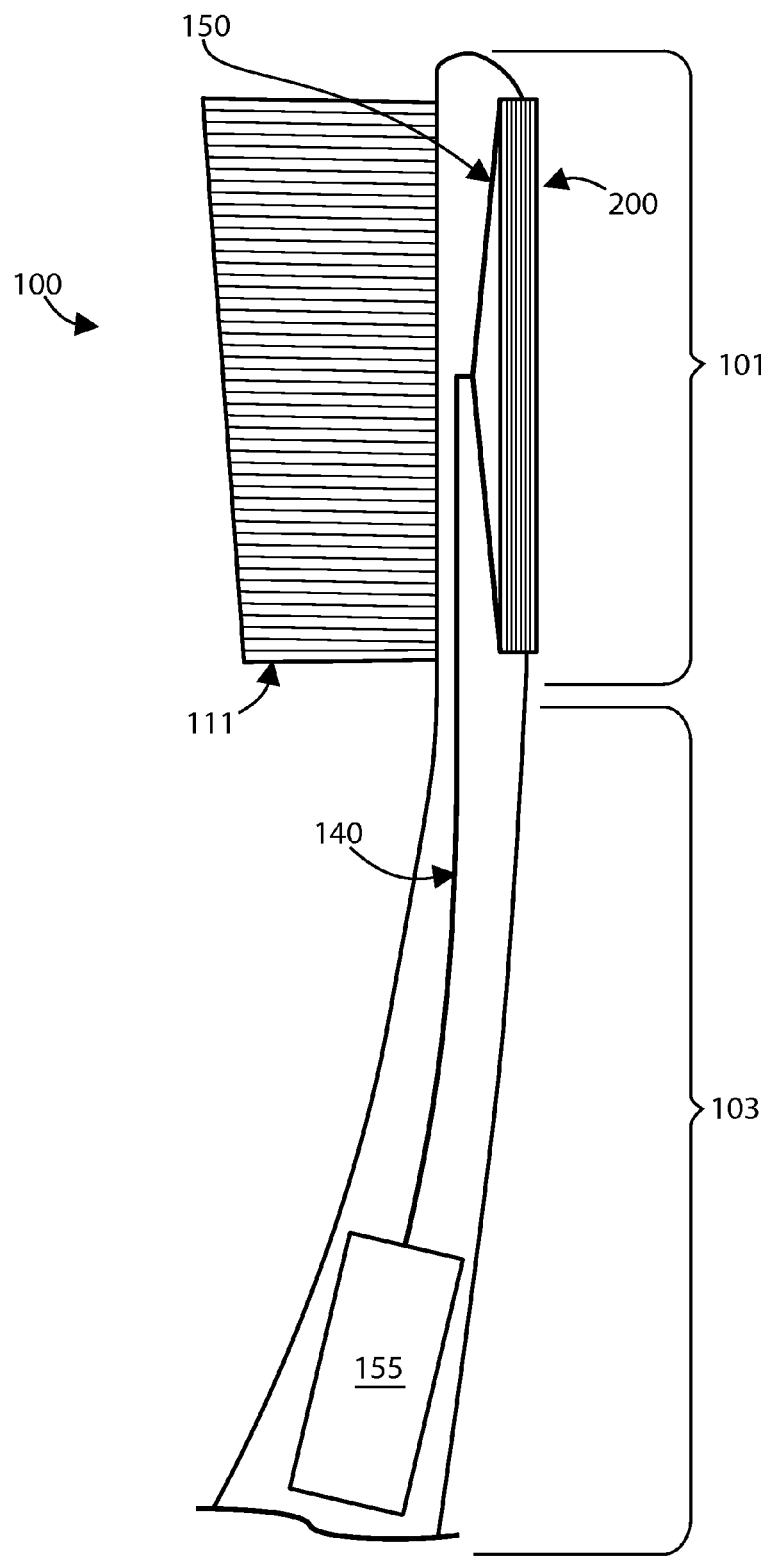
FIG. 3 is a schematic fragmentary cross-sectional illustration of a toothbrush construction according to an embodiment of the invention.

FIG. 3 schematically illustrates a toothbrush 100 having a collecting member 200 and a reservoir 155 provided for storing an oral fluid medium, such as saliva and/or a mixture of saliva and dentifrice. In various constructions, the reservoir 155 can be provided in the neck portion 105 of the toothbrush 100 or at the distal end of the toothbrush handle 103.

A fluid pathway 140, such as a capillary channel, generally extends in the longitudinal direction of the toothbrush 100 for delivering oral fluid to the reservoir 155 from at least one inlet 150. The channel 140 uses capillary action to draw liquid from the inlet 150 to the reservoir 155. The capillary channel 140 generally has a capillary structure. In one construction, the channel 140 is in the form of a porous material. Examples of porous materials include fibrous materials, ceramics, and porous plastics such as those available from Porex Technologies, Atlanta, Ga. One example of a fibrous material is an acrylic material known as type number C10010, available from Teibow Hanbai Co., Ltd., Tokyo, Japan. A mixture of porous and/or fibrous materials may be provided which have a distribution of larger and smaller capillaries. The channel 140 can be formed from a number of small capillaries that are connected to one another, or as a larger single capillary tube.

It will be understood that the collected oral fluid (e.g. fluid sample) in the reservoir 155 can be analyzed for periodontal gum disease, gingivitis, plaque, halitosis (bad breath), or any other oral or general bodily disease or condition that is amenable for detection via the oral cavity of a user. The health aspects analyzed by a laboratory may include aspects related to bad health (e.g., the presence of a disease, such as indicated by the presence of a pathogen or the presence or absence of another chemical) and/or aspects related to good health (e.g., the presence of certain desirable flavanoids indicative of the activity of a breath freshener). The aspects of good health and poor health may include, but are not limited to, aspects of good and bad oral health. Poor oral health aspects may include, for example, those aspects associated with oral diseases or with poor oral care practices recognized or otherwise identified by the American Dental Association. Likewise, good oral health aspects may include, for example, those aspects associated with the lack of such oral diseases, or with oral care practices accepted by the American Dental Association. In some embodiments, a separate reservoir 155 may be provided for collected saliva.

Figure 4:
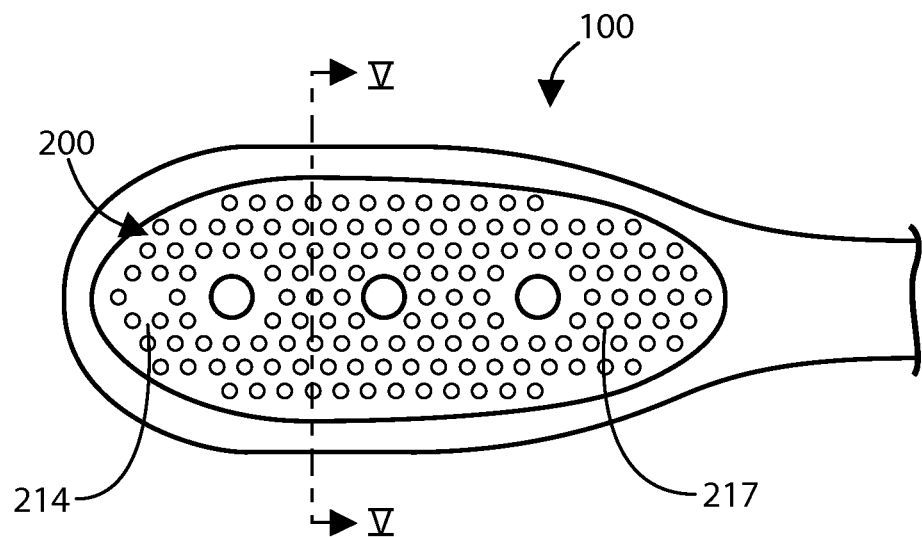
FIG. 4 is a schematic illustration of a top view of a toothbrush head construction according to an embodiment of the invention.
Figure 5:
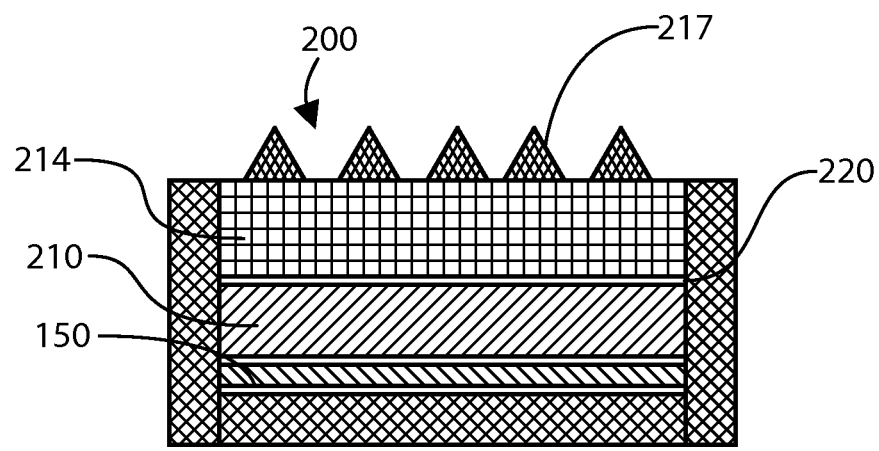
FIG. 5 is an enlarged schematic cross-sectional view of the toothbrush head construction shown in FIG. 4 taken along line 5-5.

As illustrated in FIGS. 4 and 5, the collecting member 200 includes a first layer 210 of a water insoluble porous material, such as a resin. Examples of suitable materials of the first layer 210 may include fibrous materials, ceramics, and porous plastics such as those available from Porex Technologies, Atlanta, Ga. The water insoluble material generally maintains the structure of the collecting member 200. The layer 210 of porous material can include a portion of the head 101. The collecting member 200 can be secured on or within at least one surface of the head 101 or in a basin cavity in the head 101.

A second layer 214 is positioned on the first layer 210. The second layer 214 is provided in wearable construction so that it can erode due to mechanical abrasion during use of the toothbrush 100 or it can be formed of a water-soluble material to dissolve in the oral cavity. In one construction, the second, outer layer 214 may include a water-soluble polymer (such as polyethylene oxide, polyethylene glycol, or polyvinyl alcohol). Nevertheless, other non-toxic polymer with a controllable water solubility can be used in the toothbrush. It is noted that the solubility of the polymer used in the outer layer 214 should be low enough that it dissolves out slowly, over a period of many uses. In these constructions, the collection member 200 has a first thickness which is reduced or shortened during use to a second thickness smaller than the first thickness. In some embodiments, outer layer 214 may have the property of being porous to allow transmission of fluids in the oral cavity (e.g. saliva and/or water) to underlying first layer 210 for collection in reservoir 155 on a continuing basis during use. In other embodiments, outer layer 214 may be non-porous to allow collection of fluids in the oral cavity only once layer 214 wears or dissolves away. In still yet other embodiments, outer layer 214 may be both porous and wear or dissolve with use over time.

The two layers 210, 214 can be produced either by conventional manufacturing techniques, such injection molding or extrusion. Alternatively, an extrusion construction, one layer can be extruded and then the other layer can be thermoformed/compression molded or laminated onto the extruded layer.

Figure 6:
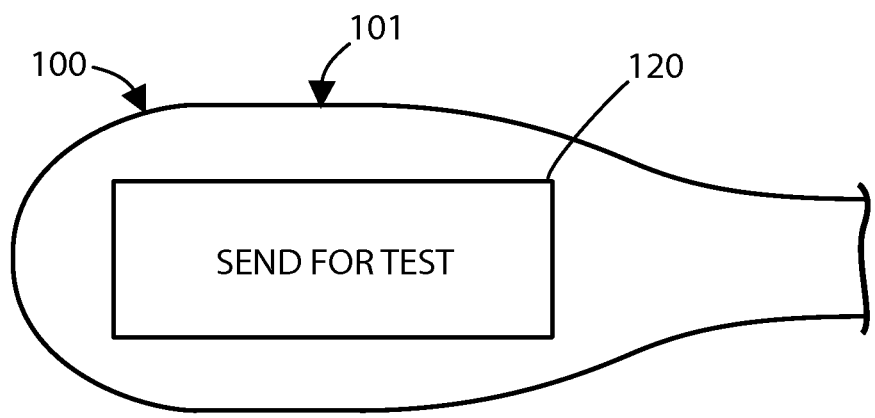
FIG. 6 is a schematic illustration of a top view of a toothbrush construction when a wearable top layer exposes an underneath layer.
Figure 7:
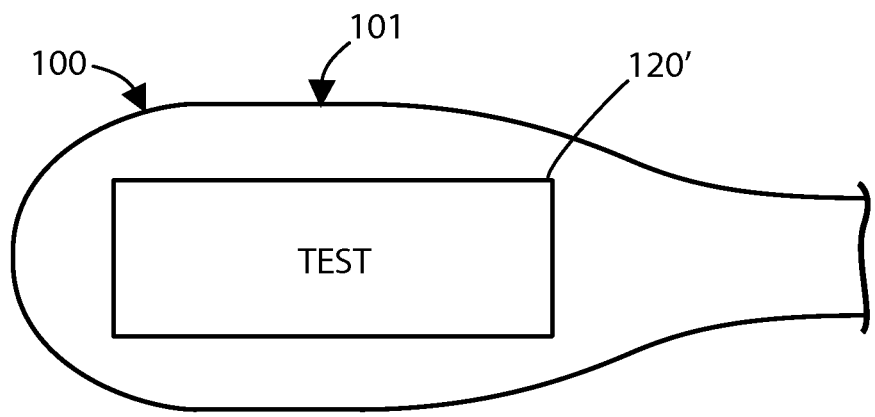
FIG. 7 is a schematic illustration of a top view of an alternative toothbrush construction when a wearable top layer exposes an underneath layer.

In one construction when the collecting member 200 comes into contact with water, saliva or a chemical in the mouth, the outer layer 214 erodes and a region of the toothbrush 100 is exposed by the eroded portion of the outer layer 214. As the outer layer 214 erodes away with repeated use, it not only exposes layer 210, but in some embodiments it also exposes indicia 120 on underlying layer 220 that indicates when the toothbrush 100 has collected and stored a predetermined amount of oral fluid in reservoir 155 sufficient to conduct a laboratory analysis and hence should be returned or sent by the user to a laboratory for testing/evaluation of the stored oral fluid in reservoir 155. In some embodiments, the indicia 120 can be a visible color that attracts the user's attention to the layer 220 and signals or illustrates the amount of effective life remaining in the toothbrush 100 and/or tells the user when the toothbrush 100 is ready for testing. Alternatively, or in addition to color indication, the indicia 120 can be a message that tells the user the same. For example, as shown in FIGS. 6 and 7, the indicia 120, 120' can be alphanumeric characters, such as without limitation "TEST" or "SEND FOR TEST". Alternatively, the indicia 120 can be a graphical symbol or icon. The symbolic aspect is particularly advantageous for providing an oral care implement for use in multiple social geographic regions without the need to translate text into different languages. It will be appreciated that any suitable color, alphanumeric or graphic indicators, or combinations thereof may be used.

The collecting member 200 can also function as a wear indicator to clearly indicate to the user of the toothbrush to forward the toothbrush for health screening or testing of collected oral fluid. The member 200 can be located at strategic position about the head 101. The collecting member 100 will provide notice to the user when the toothbrush is ready. In an illustrative embodiment, as shown in FIG. 3, the collecting member 200 is shown in a prismatic shape and located on one surface on head 101 opposite the surface containing cleaning elements 111 which could channel the saliva and/or other collected oral fluid into inlet 150 more efficiently into fluid pathway 140. However, this illustrated shape and location is not limiting. The collecting member 200 can have any appropriate shape and be located on any suitable surface(s) on the toothbrush 100 that preferably can be viewed by the user and provide oral care benefits.

The inlet 150 can be configured as a non-woven pad, membrane or other structure that allows passage of the oral fluid. Examples of materials that can be used for the inlet include porous plastics and other porous materials, such as those described below with reference to the capillary channel 140.

In one construction, the inlet 150 can be located on a surface of the head 101 generally opposite the surface that contains the tooth cleaning elements 111.

When the collection member 200 is provided for the toothbrush 100, the inlet 150 can be incorporated into the first layer 210. The second layer 214 can be provided in a wearable construction and enables gentle removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, tissue cleaning projections or elements 217 disposed on second layer 214 in some embodiments can provide for gentle engagement with the soft tissue while reaching downward into the recesses of adjacent papillae of the tongue. The projections can have a variety of shapes, such as frusto-conically shaped elements, and other shapes that taper to a narrow end and thereby resemble a cone. Alternatively, tissue cleaning elements 217 may have other shapes, such as linear ridges. In other possible constructions, the inlet 150 can be located within the field of the tooth cleaning elements 111.

Figure 9:
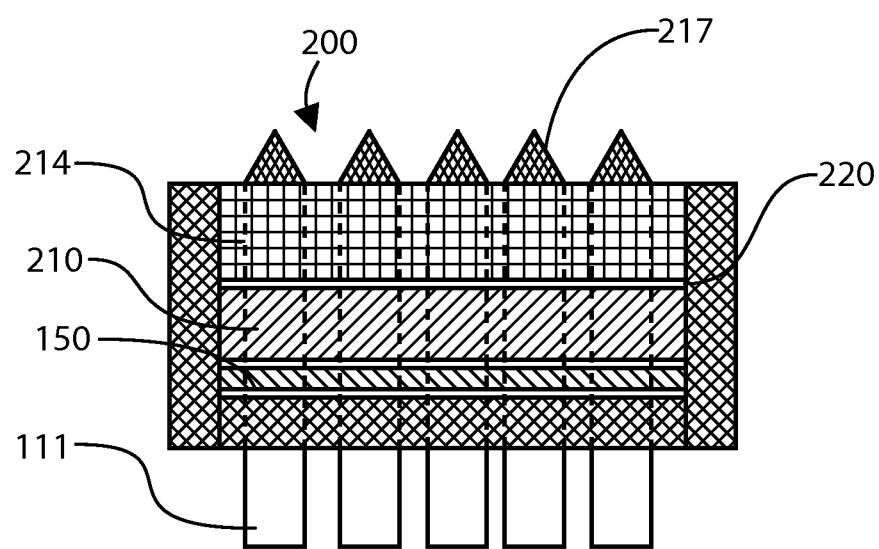
FIG. 9 is an enlarged schematic cross-section view of an alternative construction of the toothbrush head shown in FIG. 5.

In some embodiments as shown in FIG. 9, tissue cleaning elements 217 may extend completely through layers 214, 210 and connect to either tooth cleaning elements 111 and/or be formed as an integral part of the tooth cleaning elements, or alternatively tissue cleaning elements 217 may be anchored in the material near the front portion 107 of head 101 that supports tooth cleaning elements 111. These constructions may be beneficial where layer 214 is made of a material that is intended to wear or dissolve away with use over time to prevent tissue cleaning elements 217 from dislodging into the oral cavity of a user.

Optionally, a plurality of inlets may be provided on both the surface of the head 101 that contains the tooth cleaning elements as well as the opposite the surface of the head, e.g., for collecting the oral fluid at different areas of the oral cavity. The plural inlets 150 may be connected to a single fluid pathway channel 140 from opposite sides of head 101 that lead to reservoir 155.

The reservoir 155 may be formed from a suitable material and formed in a voided container construction. Alternatively, the reservoir 155 may include reticulated foam in the void space of the container, the foam may be hydrophilic. Other examples of materials that can be used for the reservoir 155 include ceramics and porous plastics.

The capillary channel 140 can be press-fit into an opening in the handle 103 or, alternatively, the handle 103 can be overmolded around the capillary channel 140. In a multiple capillary construction, the capillary channel 140 generally provides a path by which air can enter the otherwise closed reservoir 155. The finer capillaries of channel 140 transfer fluid from the inlet 150. The larger capillaries allow air to enter the reservoir 155. In general, air can enter through at least the largest capillary in the channel.

Figure 8:
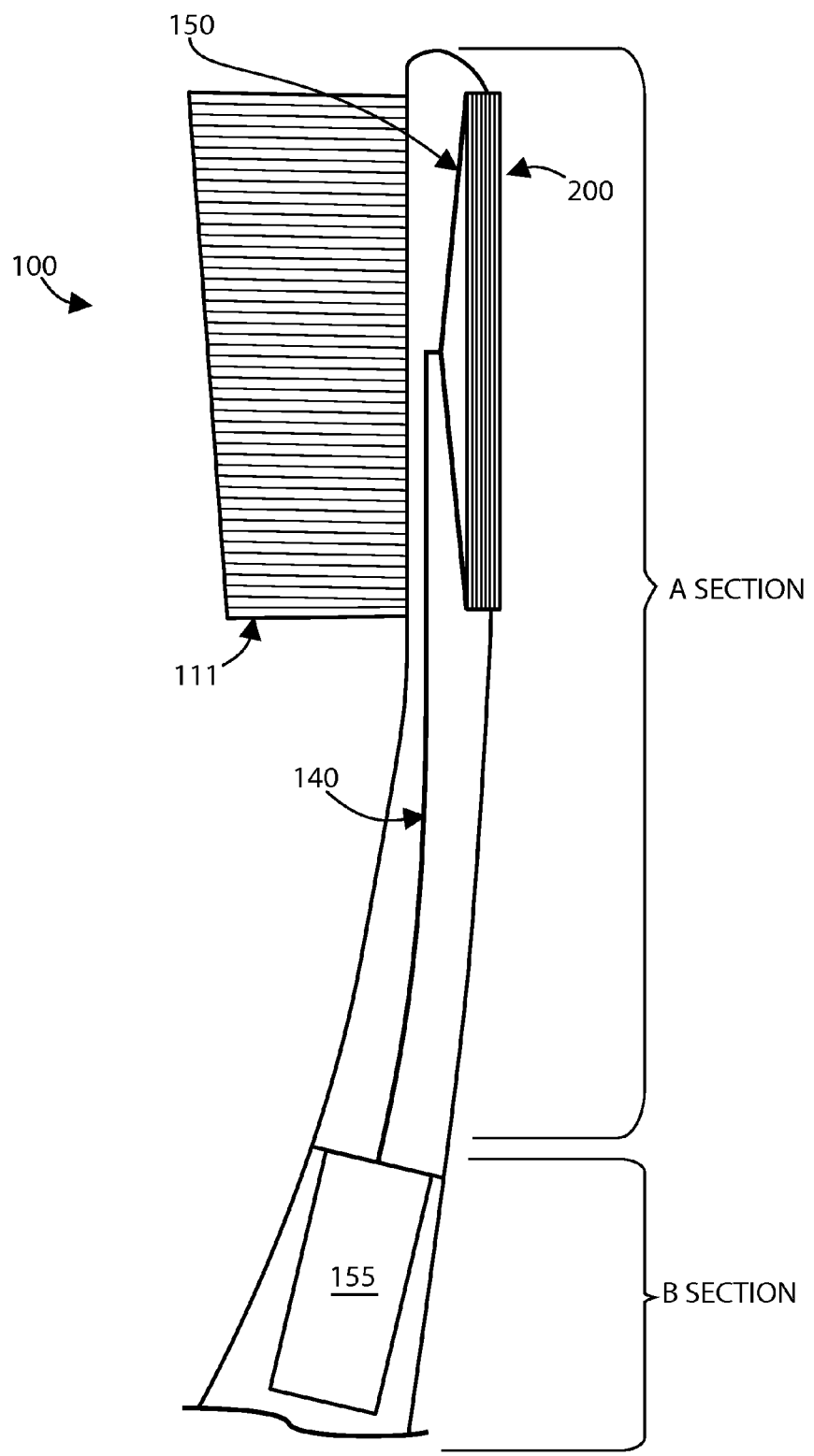
FIG. 8 is a schematic fragmentary cross-sectional illustration of an alternative toothbrush construction according to an embodiment of the invention.

In an alternative construction shown in FIG. 8, the toothbrush 100 may comprise a brush section A and a removable reservoir section B that are joined to each other, e.g., by threaded engagement, snap-fitting, or the like. The reservoir section B can be disposable, refillable, and/or interchangeable with other reservoir sections B. Alternatively, the reservoir section B can be can be replaceable, e.g., by inserting a replaceable reservoir 155 cartridge into a recess in the toothbrush. The cartridge can be spring-loaded to stay in place after insertion, and/or can have a seal to prevent unwanted leakage of oral fluid. Alternatively, the reservoir 155 may be placed at a neck location of the toothbrush 100. In some possible embodiments, the fluid collection system described herein may be incorporated into an electric-powered toothbrush. In yet other embodiments of electric toothbrushes, the toothbrush handle and/or recharging base may incorporate diagnostic circuitry which could be triggered by markers present and detected in the oral fluids collected by toothbrush 100 (e.g. plug and play). Accordingly, the fluid collection system described herein is not limited in application to only manual toothbrushes.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention and described and claimed herein.

What is claimed is:

1. An oral care implement, comprising:
   an oral care region having an oral member with a thickness which is reduced during oral use;
   a receiver coupled to the oral member for receiving an oral fluid;
   fluid pathway in communication with the receiver;
   a reservoir in communication with the fluid pathway for retaining an oral fluid;
   a plurality of tissue cleaning projections extending from the oral member for engaging oral tissue; and
   tooth cleaning elements are disposed opposing, the tissue cleaning projections;
   wherein the oral member comprises a plurality of layers, at least one layer includes the plurality of tissue cleaning projections extending therefrom for engaging oral tissue, and a layer of the oral member includes a testing indicator that identifies when the oral care implement is ready for oral id testing.

2. The oral care implement of claim 1, wherein the receiver comprises a non-woven pad or membrane.

3. The oral care implement of claim 1, wherein the reservoir comprises a replaceable cartridge.

4. The oral care implement of claim 1, further comprising a first section containing the oral care region and the fluid pathway, and a second section containing the reservoir, wherein the second section is releasably attached to the first section.

5. The oral care implement of claim 1, wherein the fluid pathway includes a fibrous material, ceramic, porous plastic, or combination thereof, for providing capillary recovery of an oral fluid.

6. The oral care implement of claim 1, wherein the oral member comprises a first layer, a second, soluble layer that erodes away to expose said first layer, and indicia that indicates when the reservoir should be provided for testing.

7. An oral care implement, comprising:
   a collection member for collecting an oral fluid;
   a reservoir for storing the oral fluid;
   a fluid pathway fluidly connecting the collection member with the reservoir to provide the oral fluid to the reservoir;
   at least one indicia that provides an indication when a predetermined amount of oral fluid is stored in the reservoir;
   a plurality of tissue cleaning projections extending from the oral member for engaging oral tissue; and tooth cleaning elements are disposed opposing the tissue cleaning projections;

wherein the collection member includes a layer positioned above the indicia that covers the indicia below.

8. The oral care implement of claim 7, wherein the reservoir comprises a replaceable cartridge.

9. The oral care implement of claim of 7, further comprising a receiver coupled to the collection member for receiving the oral fluid.

10. The oral care implement of claim 9, further comprising a first section containing the oral care region and the fluid pathway, and a second section containing the reservoir, wherein the second section is releasably attached to the first section.

11. The oral care implement of claim 7, wherein the fluid pathway includes a fibrous material, ceramic, porous plastic, or combination thereof, for providing capillary recovery of an oral fluid.

12. The oral care implement of claim 7, wherein the layer is comprised of a material that gradually wears or dissolves away during use to expose the indicia below the layer.

13. The oral care implement of claim 7, wherein the layer is made of a water-soluble polymer.

14. The oral care implement of claim 7, wherein the indicia is selected from the group consisting of colors, alphanumeric characters, graphic symbols, and combinations thereof.

15. The oral care implement of claim 7 wherein the implement is a electric toothbrush.

16. The oral care implement of claim 7 wherein the oral care implement comprises a neck and the reservoir is positioned in the neck.

* * * * *